US008706517B2

(12) United States Patent
Rowe et al.

(10) Patent No.: US 8,706,517 B2
(45) Date of Patent: Apr. 22, 2014

(54) MEDICAL PRACTITIONER PEER REVIEW SYSTEM AND METHOD

(75) Inventors: Andrew G. Rowe, Portland, OR (US); Samuel P. Freedman, Portland, OR (US)

(73) Assignee: AllMed Healthcare Management, Inc., Portland, OR (US)

(*) Notice: Subject to any disclaimer, the term of this patent is extended or adjusted under 35 U.S.C. 154(b) by 1112 days.

(21) Appl. No.: 12/276,014

(22) Filed: Nov. 21, 2008

(65) Prior Publication Data

US 2010/0131282 A1    May 27, 2010

(51) Int. Cl.
| G06Q 10/00 | (2012.01) |
| G06Q 50/00 | (2012.01) |
| A61B 5/00 | (2006.01) |
| G06F 19/00 | (2011.01) |

(52) U.S. Cl.
USPC .................................................. 705/2; 705/3

(58) Field of Classification Search
USPC ................................... 705/2–4; 600/300–301
See application file for complete search history.

(56) References Cited

U.S. PATENT DOCUMENTS

| 5,544,044 | A |  | 8/1996 | Leatherman |
| 5,652,842 | A |  | 7/1997 | Siegrist, Jr. et al. |
| 5,724,379 | A |  | 3/1998 | Perkins et al. |
| 5,924,073 | A |  | 7/1999 | Tyuluman et al. |
| 6,078,894 | A |  | 6/2000 | Clawson et al. |
| 6,154,726 | A |  | 11/2000 | Rensimer et al. |
| 7,085,800 | B2 | * | 8/2006 | Abbott et al. ................. 709/200 |
| 2005/0177403 | A1 |  | 8/2005 | Johnson |
| 2007/0192157 | A1 | * | 8/2007 | Gooch ............................. 705/9 |
| 2007/0198296 | A1 | * | 8/2007 | Pellinat et al. .................... 705/2 |
| 2007/0288264 | A1 | * | 12/2007 | Brown et al. ..................... 705/2 |
| 2008/0104521 | A1 | * | 5/2008 | Dubinko et al. ............. 715/744 |
| 2009/0149722 | A1 | * | 6/2009 | Abolfathi et al. ............. 600/301 |

OTHER PUBLICATIONS (www.admere.com) (published on Jan. 18, 2008) (printout provided) (hereinafter referred to as AMR)—avaiable at http://www.archive.org/web/web.php.*
www.admere.com, published on Jan. 18, 2008, available at http://www.archive.org/web/web.php.*
Advanced Medical Reviews. http://www.admere.com/. 2005. Los Angeles, CA.
MD Review. http://www.md-review.com/. 2008. Ketchum, ID.
Acumentra Health. http://www.acumentra.org/. 2008. Portland, OR.

* cited by examiner

Primary Examiner — Joy Chng
(74) Attorney, Agent, or Firm — Alleman Hall McCoy Russell & Tuttle LLP

(57) ABSTRACT

Systems and methods for evaluating the performance of at least one medical practitioner are provided. In one example, the method includes generating a specialty specific review form based on medical data collected from the client. The example method may further include selecting a peer review board based on the specialty of the at least one medical practitioner under review. Following selection of the peer review board, the method includes subsequently transferring the specialty specific review form to the peer review board. The method may further include receiving a peer analysis of the at least one medical practitioner from the peer review board where the peer analysis may include a completed specialty specific review form. A standardized report may be generated evaluating a level of performance of the at least one medical practitioner based upon data included in the peer analysis.

20 Claims, 13 Drawing Sheets

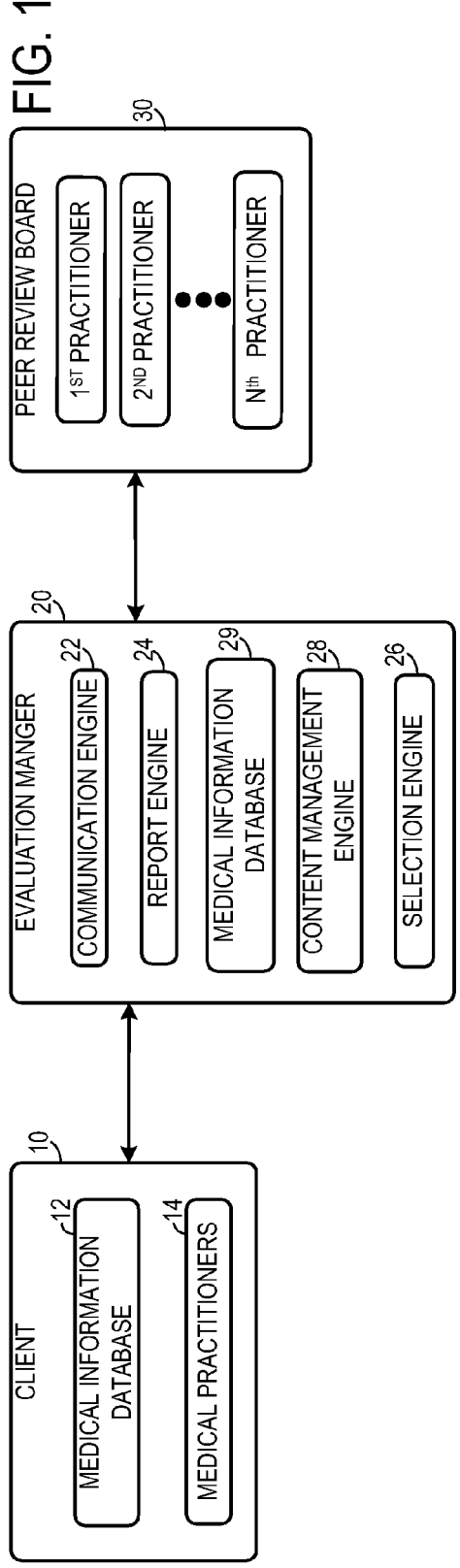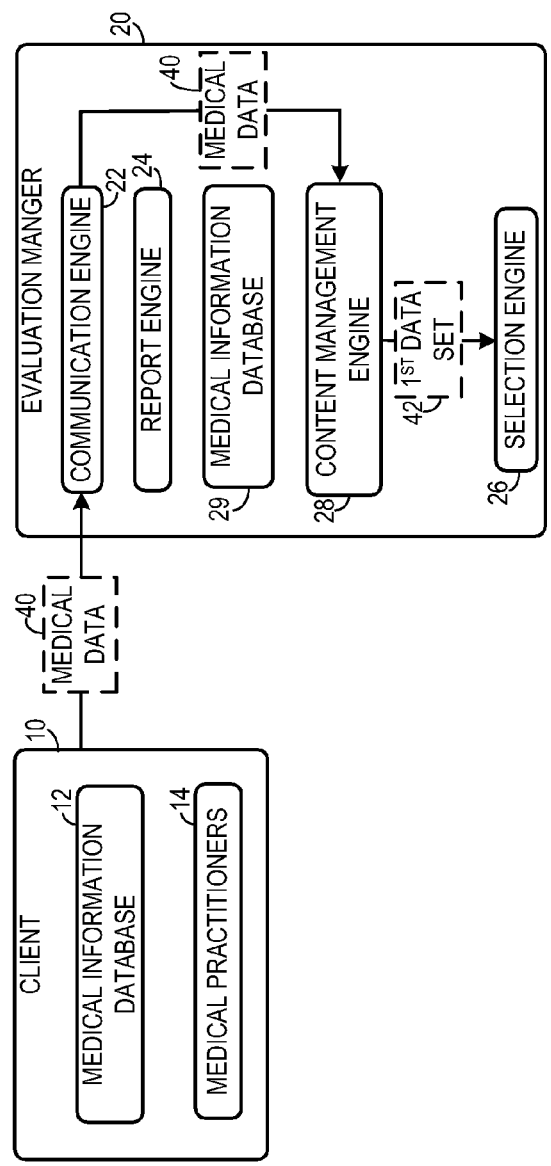

FIG. 7A

General Surgery — Reviewed By: Jacobson, Jake
Date Sent: 5/20/08
Due Date: 1/1/09

| Case # | Patient Name | Date | Practitioner | Pre-Procedure Evaluation | Procedure Technique | Complications/ Timely Recognition | Post- Procedure Care | Utilization of Ancillary Services and Consultants | Comments |
|---|---|---|---|---|---|---|---|---|---|
| 1 | James Smith | 6/1/08 | Bill Watts | 718 | 718 | 718 | 718 | 718 | |
| 2 | | | | | | | | | |
| 3 | | | | | | | | | |
| 4 | | | | | | | | | |

| Score | Description | Color |
|---|---|---|
| 1 | Standard of Care was met in all regards | |
| 2 | Standard of Care was met, but with some concerns | |
| 3 | Standard of Care was not met, with risk of negative outcome | |
| 4 | Standard of Care was not met with negative outcome | |

FIG. 7B

Reviewed By: Manning, Steve
Date Sent:10/20/08
Due Date:1/1/09

Cardiology/Cardiovascular
Review Range: 1/1/2008-3/1/2008 ← 752

Catheterizations ← 750

| Case # | Patient Name | Date | Practitioner | Pre-procedure Evaluations and Indications | Procedure Conduct | Complications/ Timely Recognition | Comments |
|---|---|---|---|---|---|---|---|
| 1 | Brown, Cinnamon | 1/1/08 | Adams, Sally | ▨ | ▨ | ▨ | |
| 2 | Davis, Reid | 2/1/08 | Adams, Sally | ▨ | ▨ | ▨ | |
| 3 | Same, Sam | 2/20/08 | Adams, Sally | ▨ | ▦ | ▨ | |
| 4 | Wall, Charles | 3/1/08 | Adams, Sally | ▤ | | | |

↙ 710   ↙ 712   718 (callouts)   715

| Score | Description |
|---|---|
| 1 | Standard of Care was met in all regards |
| 2 | Standard of Care was met, but with some concerns |
| 3 | Standard of Care was not met, with risk of negative outcome |
| 4 | Standard of Care was not met with negative outcome |

↙ 714

Color legend: 715

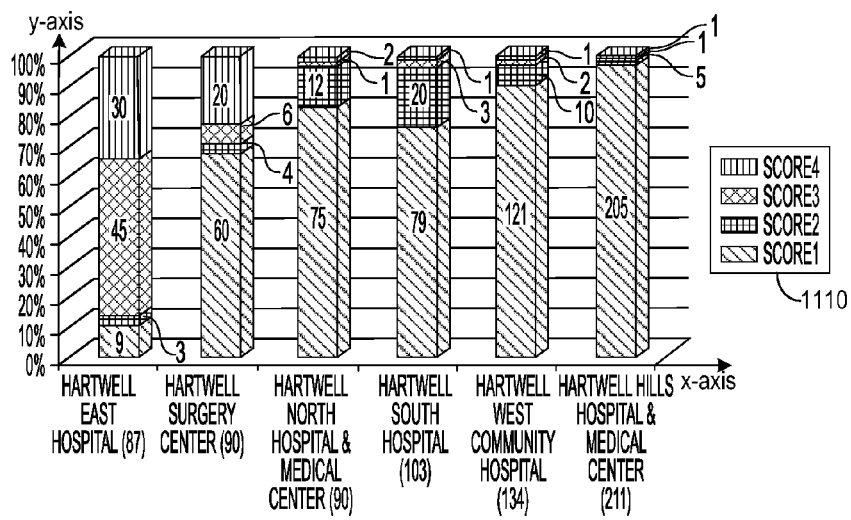
FIG. 11
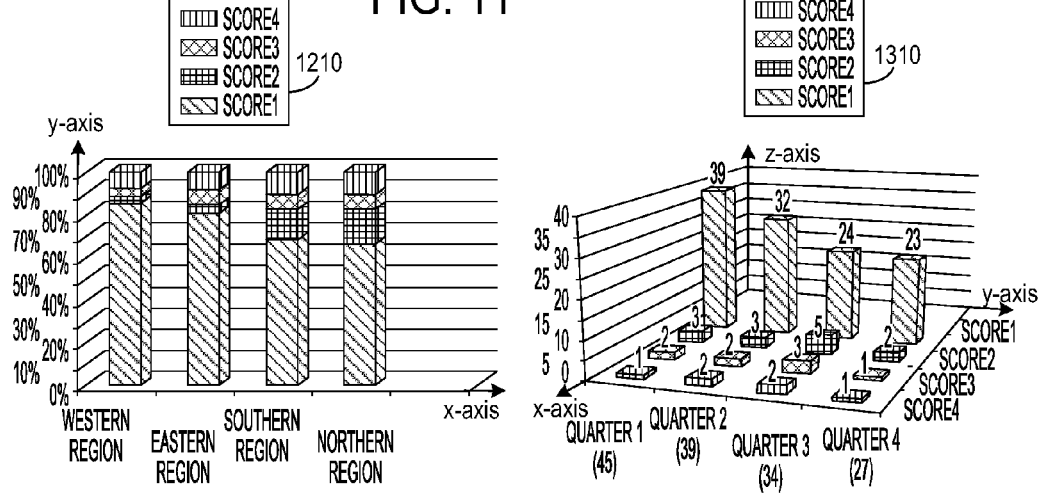
FIG. 12
FIG. 13
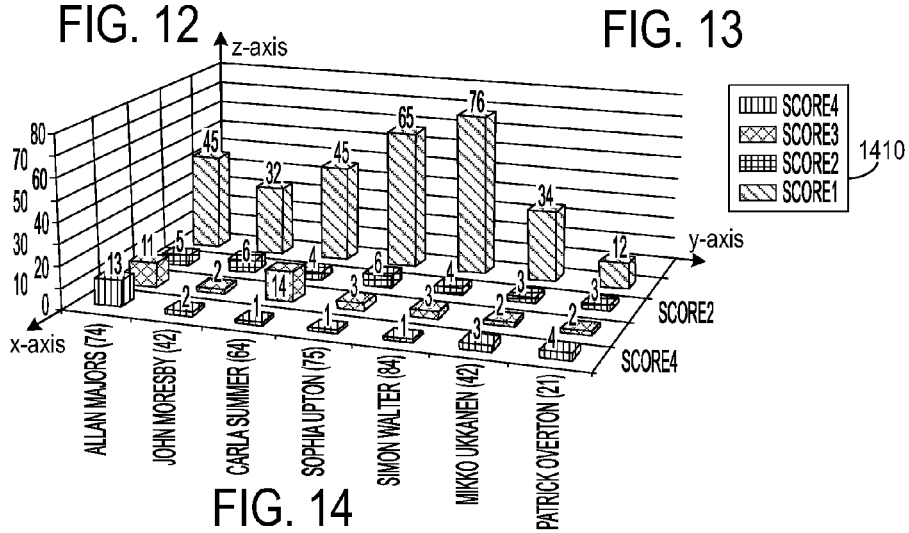
FIG. 14

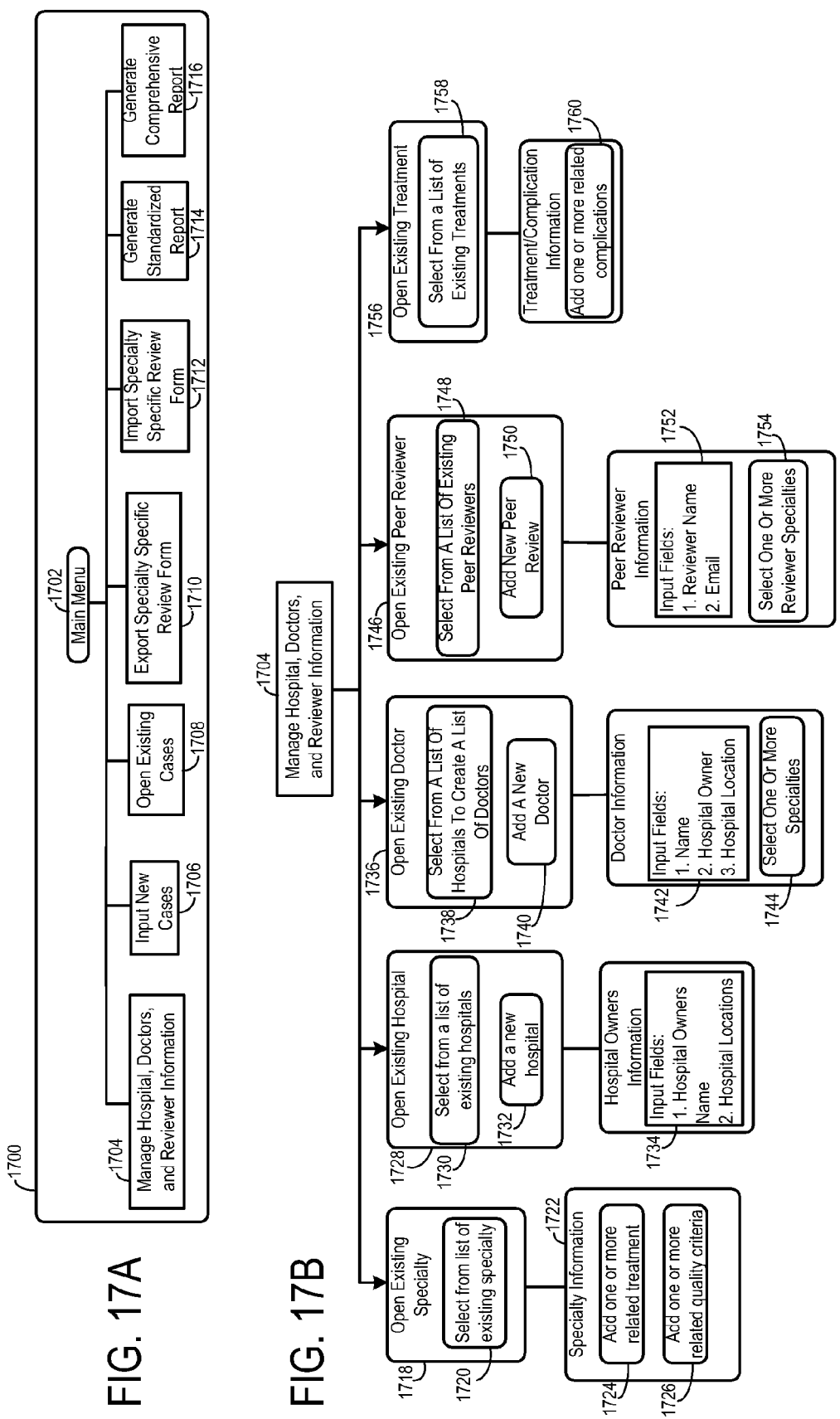

MEDICAL PRACTITIONER PEER REVIEW SYSTEM AND METHOD

BACKGROUND

Peer-based review of medical practitioners has been used in the medical community for decades to generate a substantive review of a practitioner's performance level as well as to assess the level of care which the practitioner has provided. Many peer-based reviews are carried out in response to a medical error (e.g. medical malpractice or misconduct), hindering preventative actions from being taken to avoid medical errors. Furthermore, the duration of a peer-based review may be lengthy due to the large amount of medical data under evaluation as well as the inefficient data management of the organization conducting the review. It is for this reason that many health care organizations are seeking fast and efficient methods of practitioner review.

Attempts have been made, by some health care organizations, to utilize automated statistical analysis to provide fast and efficient assessment of medical practitioners. However, generating substantive reviews of medical practitioners from computerized statistical analysis methods may be difficult due to the complexity of the medical system. Further, such analysis may be limited in its value as the analysis is generally based primarily on statistical inputs. By using computerized statistical analysis without any substantive peer review, health care organizations have been able to increase the efficiency of practitioner review and decrease the cost. However, such efficiency has resulted in sacrificing the quality of the review.

SUMMARY

Accordingly, various exemplary embodiments related to efficient generation of a substantive medical evaluation of a medical practitioner are provided. For example, a method for evaluating the performance of one or more medical practitioners associated with a client is provided. In an example method, a specialty specific review form is generated based on medical data collected from the client. A peer review board may be selected based on the specialty of one or more medical practitioners under review and the specialty specific review form may be transferred to the peer review board. The method may further include receiving a peer analysis of one or more medical practitioners, where the peer analysis may include a completed specialty specific review form. A standardized report may be generated evaluating a level of performance of one or more medical practitioners based upon data included in the peer analysis.

In this way, a substantive review, including a peer analysis, of one or more medical practitioners may be quickly and efficiently generated.

BRIEF DESCRIPTION OF THE DRAWINGS

FIG. 1 shows a client, an evaluation manager, and a peer review board.

FIGS. 2-6 illustrate workflow diagrams, which may be carried out by the client, evaluation manager, and peer review board, shown in FIG. 1.

FIGS. 7A-7B illustrates specialty specific review forms which may be generated by the evaluation manager, shown in FIG. 1.

FIGS. 10-14 show various reporting charts that may be included in a comprehensive reporting package.

FIGS. 17A-17C illustrate a management application and the corresponding architecture.

DETAILED DESCRIPTION

Figure 3A:
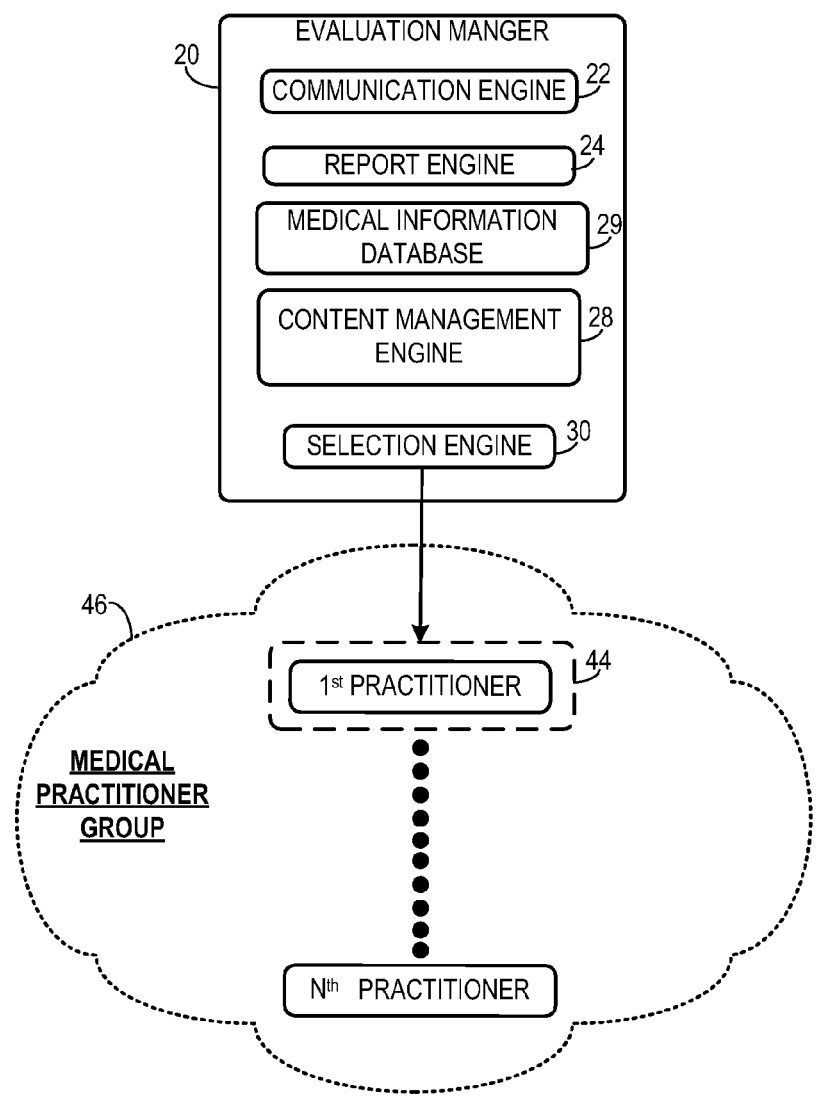

As described in more detail below, systems and methods for generating a standardized evaluation of at least one medical practitioner based on a peer analysis are provided. The following description provides examples of a medical practitioner peer review system and method, but the disclosure is not intended to be limited by such examples and such examples are provided only for illustrative purposes.

In a first example, FIG. 1 illustrates a client 10, an evaluation manager 20, and a peer review board 30 in communication. Various suitable types of communication systems may be utilized, alone, and/or in combination, to communicatively link the client, the evaluation manager and the peer review board. For example, communication systems may include in part or in whole, a web-based communication system, computer networks, private or public networks, a fax network, a courier, and/or a mail service (e.g. US Postal Service, Federal Express, etc.). Through the communication link, evaluation manger 20 may be adapted to generate a substantive evaluation of a medical practitioner associated with the client via the peer review board, discussed in greater detail herein with regard to FIGS. 2-6.

Client 10, evaluation manger 20 and peer review board 30 are communicatively linked to enable generation of a standardized report, discussed in more detail herein. Client 10 may be a health care organization, such as a Health Maintenance Organization HMO, a medical facility such as a hospital, a care facility, a practitioner group, etc. In some examples, client 10 may be any organization or individual requesting a peer review evaluation of a medical practitioner. Further, in some examples, the evaluation manager and/or the peer review board may be associated (e.g. employed) with the client. However, in other examples the client, evaluation manager, and the peer review board may be separate entities.

In some examples, client 10 may include or may be communicatively linked to a client-side medical information database 12 or a filing system. The client-side medical information database or filing system may include medical records, such as medical files documenting a specific medical practitioner's course of treatment of a patient and/or patient histories. The medical files may include identification data, such as patient names, admission dates, professional's names (i.e. doctor), professional's specialties, hospital owner(s), hospital locations, hospital regions, etc., as well as charts, procedural data, practitioner analysis', created by various personnel associated and/or employed by the client. The personnel associated and/or employed by the client may include medical practitioners, nurses, staff, etc. In one example, the client-side medical information database may include an electronic storage system comprising one or more computing devices having a processor and readable memory. Additionally or alternatively, the client-side medical information database may include a hard-copy filing system containing paper copies of the medical files.

In some examples, such as where the client is a health care organization, the client may include medical practitioners 14, which may be highly skilled. As an example, highly skilled medical practitioners may include trained medical practitioners, including, but not limited to, anesthesiologists, cardiologist, surgeons (e.g. general surgeons, neurosurgeons, etc.), pathologists, emergency room (ER) doctors, urologists, pathologists, radiologists, hospitalists, general practitioners, obstetricians, gynecologists, etc.

Client 10 may request an evaluation of one or more medical practitioners 14, associated with the client, from evaluation manager 20. In some examples, the request may be proactive. A proactive request may include a request for an evaluation of one or more medical practitioner without provocation due to a medical error. A medical error may include a misdiagnosis, an improper course of treatment, medical malpractice or misconduct allegations, etc. In this way, an evaluation of a medical practitioner may be performed prior to a medical error, allowing preventative actions to be taken to improve the medical practitioner's standard of care, thereby diminishing the chance of future medical errors.

In the illustrated example, evaluation manager 20 may include sub-systems, including but not limited to a communications engine 22, a report engine 24, a selection engine 26, and a content management engine 28. Such sub-systems are discussed in greater detail herein with regard to FIGS. 2-6. The aforementioned sub-systems may work in conjunction to select the peer review board 30 and generate a standardized report, assessing the performance of a medical practitioner associated and/or employed by the client, based on a peer analysis. Assessment of the performance of a medical practitioner may include review of practitioner decisions via a scoring or grading system, such a numerical scoring system.

In the illustrated example, the evaluation manager may further include a manager-side medical information database 29 adapted to store the standardized report generated by evaluation manager 20. Additionally, manager-side medical information database 29 may be adapted to store additional information, such as medical information including medical care benchmarks, information regarding one or more clients and/or medical practitioners associated with the client(s), etc. Manager-side medical information database 29 may be used to generate additional analysis regarding a practitioner's performance and/or a client's performance.

As illustrated, evaluation manager 20 may further be linked with peer review board 30. As described in more detail below, the peer review board may include a one or more medical practitioner's which may be selected based on their specialties. Selection of the peer review board and management of the peer review analysis may be conducted by the evaluation manager 20.

FIGS. 2-6 illustrate a number of exemplary workflow diagrams, which may be used by evaluation manager 20 to facilitate quick and efficient generation of a standardized report, evaluating the level of performance of one or more medical practitioners associated with client 10. In other examples, additional or alternate workflow diagrams may be used by the evaluation manager to facilitate quick and efficient generation of a standardized report.

As shown in FIG. 2, in response to a request, which may be proactive, for an evaluation or review of one or more medical practitioners, from client 10, evaluation manger 20 gathers medical data 40 from the client. The medical data may include charts, case notes, post operation reports, personal health records, x-rays, etc. In some examples, the medical data may be selectively and/or systematically gathered according to a scheduling algorithm. The scheduling algorithm may include an algorithm adapted to gather medical data at time intervals, which may be pre-determined. For example, a client may request a yearly evaluation for a plurality medical practitioners. Therefore, medical data may be gathered from the client once a year. In alternate examples, other suitable methods may be used to gather the medical data.

Medical data 40 may include medical files corresponding to a number of medical practitioners, such as the medical practitioner(s) under review (e.g. evaluation). In some examples, the dates corresponding to the medical files may fall within a range of dates for review requested by the client. The medical files may include identification data such as patient names, admission dates, practitioner names, a practitioner's specialty, owner of the health care organization, health care organization location, health care organization region, etc. The medical data may further include charts, diagnoses, analyses, and procedural information, corresponding to one or more medical practitioners. Thus, pertinent medical information, regarding the medical practitioner(s) under review, may be efficiently gathered, thereby increasing the efficiency of the evaluation manager.

In some examples, upon receipt of medical data 40, evaluation manager 20 may send the medical data to content management engine 28 via communications engine 22. However, in other examples another suitable sub-system, included in or associated with the evaluation manager, may send the medical data to the content management engine. The communications engine may be adapted to send medical data, to additional targeted recipients, such as selection engine 26, include in evaluation manager 20, peer review board 30, and client 10.

In some examples, an internal communications engine may facilitate communication between the sub-systems of the evaluation manager and an external communications engine may facilitate communication between entities exterior to the evaluation manager, such as the client and the peer review board. Further, in some examples, the external communications engine may use a web-based communications system and the internal communications engine may utilize an internal computer network, such as a suitable relational database management system (e.g. SQL Server). However, it can be appreciated that the internal and/or the external communications engines may utilize alternate suitable communication systems.

Content management engine 28 may be adapted to modify medical data 40, allowing the medical data to be easily viewed and analyzed by the peer review board, the client, and the sub-systems of the evaluation manager. In some examples, modification of the medical data by the content management engine may include entering the medical data into a suitable database, such as manager-side medical information database 29, re-organizing the medical data, removing elements from the medical data, and/or adding elements to the medical data. The data modified by the content management engine may be organized to form one or more data sets (e.g. data sub-sets).

In some examples, a culling system may be included in content management engine 28. However, in other examples, the culling system may be included in another suitable sub-system in the evaluation manager, such as the selection engine. The culling system may include an administrative division and a software application. The administrative division may include one or more personnel associated with or employed by the health care organization, discussed in more detail herein with regard to FIGS. 16-17C. The culling system may be configured to filter and/or modify the medical data into a data set or data sub-set, removing extraneous information. The extraneous information may include information which is not pertinent to the evaluation, such as doctor's notes, billing forms, internal administrative forms, etc. In this example, the culling system includes a computer application and imaging system allowing a user (e.g. the administrative division) to upload image files of the medical data and use the graphical representations, such as thumbnails, to re-organize or delete the image files via a suitable method, such as clicking and dragging in a Graphical User Interface (GUI). In this way the administrative division can quickly filter the medical data. However, in other examples, the culling system may be completely automated. For example, an algorithm may be used to filter out extraneous medical data. The culling system facilities quick and efficient analysis of the medical data by an administrative division due to the removal of extraneous information. It can be appreciated that in alternate examples, other suitable software applications and/or personnel may be used by the content management engine to modify the medical data.

Subsequent modification of the medical data via the content management engine, a first data set 42 may be formed by the content management engine and sent to the selection engine 26. The first data set may include medical data regarding the medical practitioner(s) under review, such as the specialty of the practitioner, treatment data, procedural data, etc., allowing the selection engine to perform a selection of an appropriate peer review board, based on the medical practitioner under review. In alternate examples, the medical data may first be sent to manager-side medical information database 29 and then transferred to the selection engine 26.

In one example, selection engine 26 may include a group of personnel associated with or employed by the evaluation manager. The personnel may include medical practitioners, such as clinicians, who may be highly skilled. However, in other examples, the selection engine 26 may be an automated system such as a software application configured to select a peer review board.

Figure 3B:
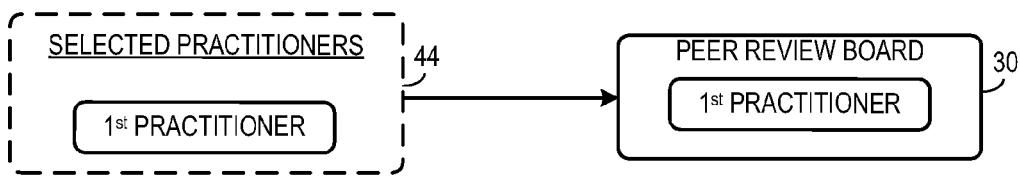

As shown in FIG. 3A, selection engine 26 may be adapted to select one or more medical practitioners 44 from a group of medical practitioners. As discussed above, the medical practitioners may be highly skilled and may be selected based on various factors, such as the specialty, location, and level of experience. In some examples, the reviewing medical practitioner(s) may be external to client 10, allowing an impartial and un-biased analysis of the medical practitioner under review, to be performed. As illustrated in FIG. 3B, a single selected reviewing medical practitioner 44 may form peer review board 30. However, it can be appreciated that in alternate examples, the peer review board may include two or more selected reviewing medical practitioners.

Figure 4:
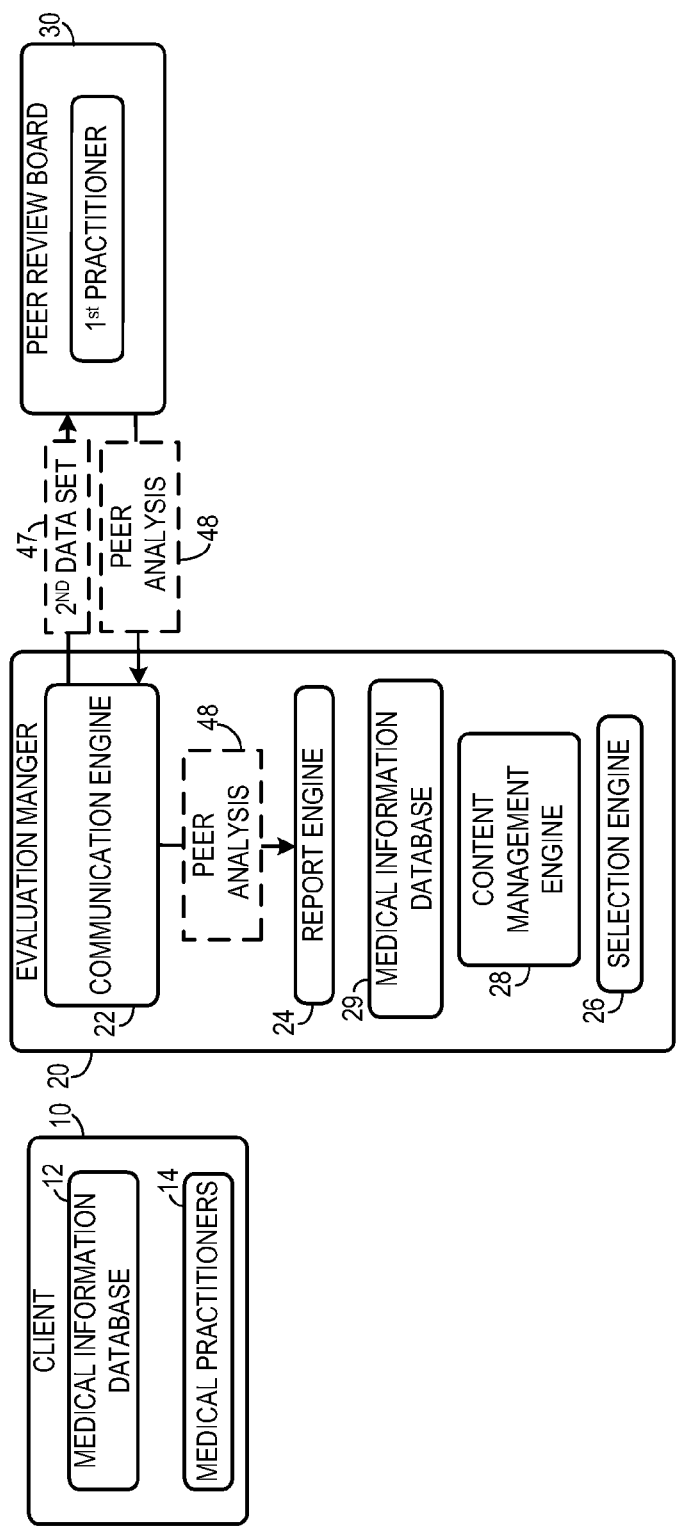

Subsequent to selection of peer review board 30, a second data set 47, generated by the content management engine, may be sent to the peer review board, as illustrated in FIG. 4. In some examples, the second data set may include medical data corresponding to the medical practitioner(s) under review. Additionally, the second data set may include a specialty specific review form generated by content management engine 28, a document outlining review guidelines for review, as well as other pertinent information concerning the medical practitioner under review. The specialty specific review form may include various review criteria tailored to the specialty of the medical practitioner under review. The review criteria may correspond to specific procedures and treatments frequently carried out in the medical specialty. Alternatively, in some examples, the review criteria may correspond to specific procedures/treatments which the medical practitioner has carried out.

In some examples, the peer review board may be prohibited from viewing medical information that does not correspond to the medical practitioner(s) under review by the peer review board. In this way, the anonymity of both the medical practitioner under review as well as their patients is assured.

An exemplary specialty specific review form 700 is illustrated in FIG. 7A. In this example the specialty of the medical practitioner is general surgery. However, it can be appreciated that alternate specialties may be used, discussed in greater detail herein. Further in this example, the specialty specific review form is a spreadsheet. However, in other examples, the specialty specific review form may be a paper document, a web form, or a Portable Document Format PDF file. The specialty specific review form may include a number of specialty specific review criteria 702. In this example, the specialty specific review criteria may include pre-procedure evaluation and indications, procedure technique, complications/timely recognition, post-procedure care, and utilization of ancillary services and consultants. However, it can be appreciated that in other examples, the specialty specific review criteria may be modified. Additionally, a number of non-specialty specific review information 704 may be included in the review form, such as reviewer's comments, the medical practitioner's name, the patient's name, and the reviewer's name.

The medical practitioners included in the peer review board may score or grade the medical practitioner's (e.g. physician's) performance in each case, based on the criteria. A set of guidelines 710, may be included in the specialty specific review form. The set of guidelines allows the peer review board, to understand the specific scoring method which should be used to complete the specialty specific review form. A description 712 of the guidelines illustrating the levels of performance, corresponding to numerical scores 714, may be included in the specialty specific review form. In this example, the levels of performance correspond to standards of care. Furthermore, additional guidelines may be provided for the peer review board, in other examples.

Depending on the configuration of the specialty specific review form, coding elements 715, such as patterns and/or colors may be assigned to each level of performance. In this example, color coding is used. However, it can be appreciated that other coding elements may be used. The peer review board may use these guidelines to determine a medical practitioner's performance level (e.g. score) for each of the specialty specific review criteria for each case. The client may also use the guidelines as a visual reference when reviewing the completed specialty specific review form. In some examples, a medical practitioner, included in the peer review board, may input a score into a field associated with a specific case and review criteria, thereby populating the field with coding elements 715, such as color coding elements. In other examples, the medical practitioner(s) included in the peer review board may simply write in the score associated with the level of performance of the medical practitioner for each criteria and case.

FIG. 7B illustrates an additional specialty specific review form 750 which may be used by the peer review board. The specialty specific review form may share some common elements with specialty specific review form 700, therefore similar parts are labeled accordingly. In this example, the specialty is cardiology/cardiovascular medicine. Further in this example, a number of catheterization procedures are reviewed. However, it can be appreciated that other treatments and/or procedures may be included in the form. The specialty specific criteria 702 for Cardiology/Cardiovascular medicine may include pre-procedure evaluation, procedure technique, and complications/timely recognition. Additional information 704 which may be included in the specialty specific review form includes the patients name, date of treatment/procedure, the medical practitioner under review, as well as a comments section. As previously discussed a description 710 of the guidelines illustrating the levels of performance, corresponding to numerical scores 714 and/or coding elements 715, may be included in the specialty specific review form. Further, in this example, the review form may include a range of dates 752 of evaluation.

In some examples the same criteria may be used to score each procedure/treatment associated with each specialty. However, in other examples the criteria may be adjusted depending on the specific procedure/treatment under review.

An exemplary table showing the review criteria for a number of specialties is given below.

TABLE 1

Specialty Specific Criteria

| SPECIALTY | CRITERIA |
| --- | --- |
| Anesthesiology | Case Conduct |
|  | Drug Selection |
|  | Pre-procedure evaluation and ASA |
|  | Charting |
|  | Extubation and Post Care |
| Bariatric Surgery | Utilization of ancillary services and consultants |
|  | Post-procedure care |
|  | Complications/Timely Recognition |
|  | Procedure Technique |
|  | Pre-procedure evaluation and indications |
| Cardiology/ Cardiovascular | Pre-procedure Evaluation and Indications |
|  | Procedure Technique |
|  | Complications/Timely Recognition |
| Emergency Medicine | Quality of History and Physical |
|  | Follow-up Instructions and Interval |
|  | Appropriate Treatment |
|  | Diagnosis Supported by Chart |
|  | Appropriate Testing |
| Endoscopy | Complications/Timely Recognition |
|  | Post-procedure care |
|  | Pre-procedure evaluation and indications |
|  | Utilization of ancillary services and consultants |
|  | Procedure Technique |
| General Surgery | Procedure Technique |
|  | Post-procedure care |
|  | Complications/Timely Recognition |
|  | Utilization of ancillary services and consultants |
|  | Pre-procedure evaluation and indications |
| Hospitalist | Appropriate Testing |
|  | Appropriate Consultations |
|  | Appropriate Response to change in Condition. |
|  | Timeliness Arrival to First Visit |
| Neurosurgery-Brain | Procedure Technique |
|  | Complications/Timely Recognition |
|  | Post-procedure care |
|  | Pre-procedure evaluation and indication |
|  | Utilization of ancillary services and consultants |
| Neurosurgery-Spine | Utilization of ancillary services and consultants |
|  | Post-procedure care |
|  | Procedure Technique |
|  | Pre-procedure evaluation and indications |
|  | Complications/Timely Recognition |
| OBGYN: For Delivery | Pre-delivery Evaluation |
|  | Fetal Monitoring |
|  | Case Conduct |
| OBGYN: For Surgery | Utilization of ancillary services and consultants |
|  | Post-procedure care |
|  | Complications/Timely Recognition |
|  | Procedure Technique |
|  | Pre procedure evaluation and indications |
| Orthopedic Surgery | Complications/Timely Recognition |
|  | Procedure Technique |
|  | Post-procedure care |
|  | Utilization of ancillary services and consultants |
|  | Pre-procedure evaluation and indications |
| Pathology | Quality of Specimen |
| Radiology | Quality of Radiograph |

TABLE 1-continued

Specialty Specific Criteria

| SPECIALTY | CRITERIA |
| --- | --- |
| Urology | Pre-procedure evaluation and indications |
|  | Procedure Technique |
|  | Complications/Timely Recognition |
|  | Post-procedure care |
|  | Utilization of ancillary services and consultants |

After the peer review board receives the second data set 47, from the content management engine, the peer review board may generate a peer analysis 48 of one or more medical practitioners based on the second data set. The peer analysis may be sent to evaluation manager 20 after the peer analysis is generated. In some examples, the peer analysis may include a completed specialty specific peer review form.

Further in some examples, the peer analysis may be transferred to the report engine as well as the manager-side medical information database 29 via communications engine 22. In other examples, the peer analysis may be directly transferred to the report engine as well as the manager-side medical information database 29.

Figure 5:
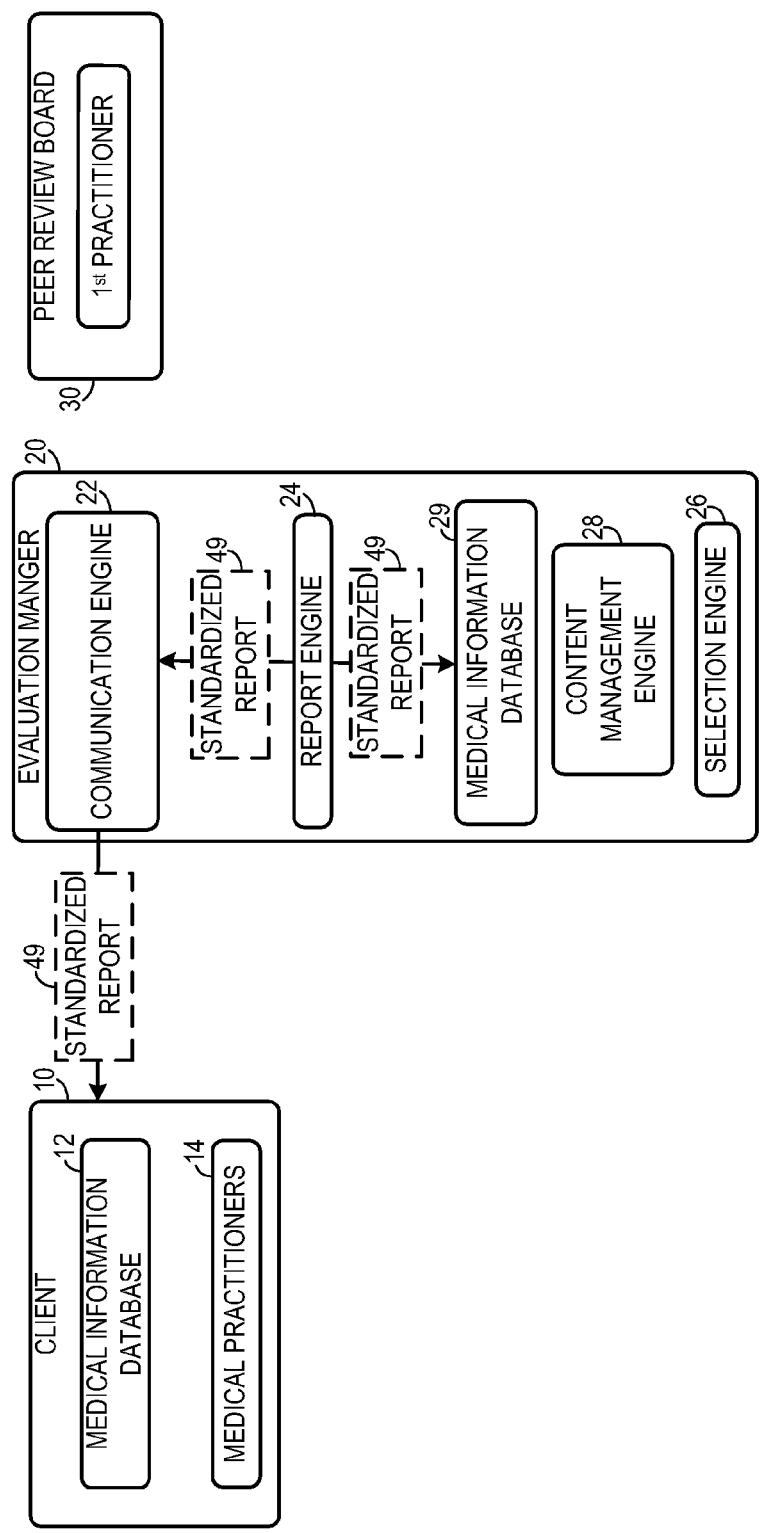

After report engine 24 receives the peer analysis, the report engine may generate a standardized report 49 shown in FIG. 5. The standardized report may include an evaluation of a level of performance of at least one medical practitioner under review based on peer analysis 48.

The standardized report may include a number of reporting charts showing (i.e. depicting) a practitioner's level of performance based on the peer analysis. The reporting charts may be in a graphical or narrative format, including charts, diagrams, graphs, spreadsheets, etc. The reporting charts may include a treatment/procedure reporting charts, illustrating the practitioner's level of performance for a number of treatments/procedures and/or criteria corresponding to the treatments/procedures. In some examples, the reporting charts may integrate information from the peer analysis and the medical information database to enable evaluation of a level of performance of the reviewed medical practitioner.

Figure 8:
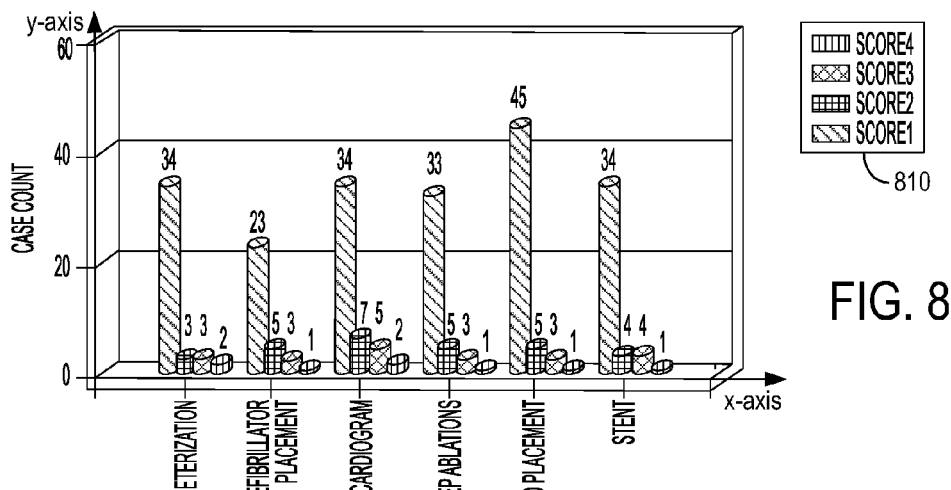
FIGS. 8-9 show various reporting charts that may be included in a standardized report.

An exemplary treatment/procedure reporting chart for a cardiologist is shown in FIG. 8. Various treatments and/or procedures performed by the medical practitioner are displayed on the x-axis. The treatments and/or procedures may include catheterization, defibrillator placement, echocardiogram, EP ablations, ICD placement, and stent. These treatments and/or procedures may vary by specialty or sub-specialty. The y-axis represents the number of procedures/treatments performed. A level of performance, documented via a color coded bar, is assigned to each treatment/procedure. The color coding corresponding to the levels of performance are shown in window 810. Alternate coding may be used, including pattern coding, etc. In this way, the client may be able to quickly and objectively assess a medical practitioner's performance. It can be appreciated that the treatment/procedure reporting chart, illustrated in FIG. 8, may be presented in another format, such as a spreadsheet or a web-based reporting system.

Figure 9:
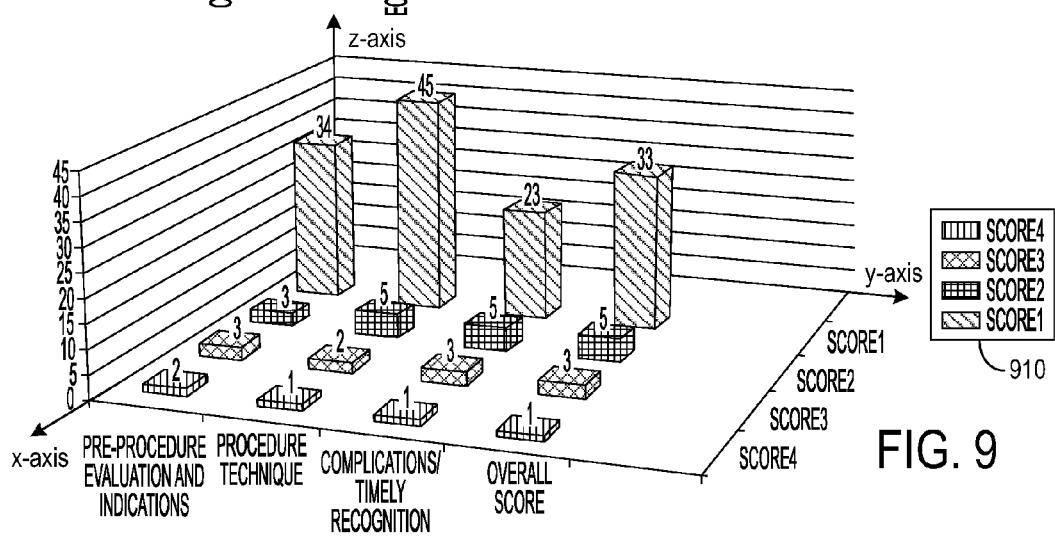

The standardized report may further include a quality criteria reporting chart, illustrating a medical practitioner's level of performance for various criteria corresponding to various treatments/procedures performed by the medical practitioner. An exemplary quality criteria reporting chart is illustrated in FIG. 9. Various criteria are displayed on the x-axis, such as pre-procedure evaluation and indications, procedure technique, complications/timely recognition, and overall score. The number of procedures/treatments performed for each criteria is shown on the z-axis and the levels of performance (e.g. score) corresponding to the procedures/treatment are offset on the x-axis. Again the levels of performance are coded, such as color-coded, allowing the graph to be easily deciphered. The correspondence between the levels of performance and the color coding is shown in window 910. It can be appreciated that in some examples, FIGS. 8 and 9 may be in the same format and the coding may correspond to enable easy identification of the performance levels.

Returning to FIG. 5, subsequent to generation of the standardized report, the standardized report may be reviewed internally by a group of internal staff associated with and/or employed by the evaluation manager. The internal review, also referred to as a quality assessment, may confirm the analysis, check for errors (e.g. grammatical and statistical errors), etc., in the standardized report. After the quality assessment is completed, the standardized report may be stored in manager-side medical information database 29, as shown in FIG. 5.

Figure 6:
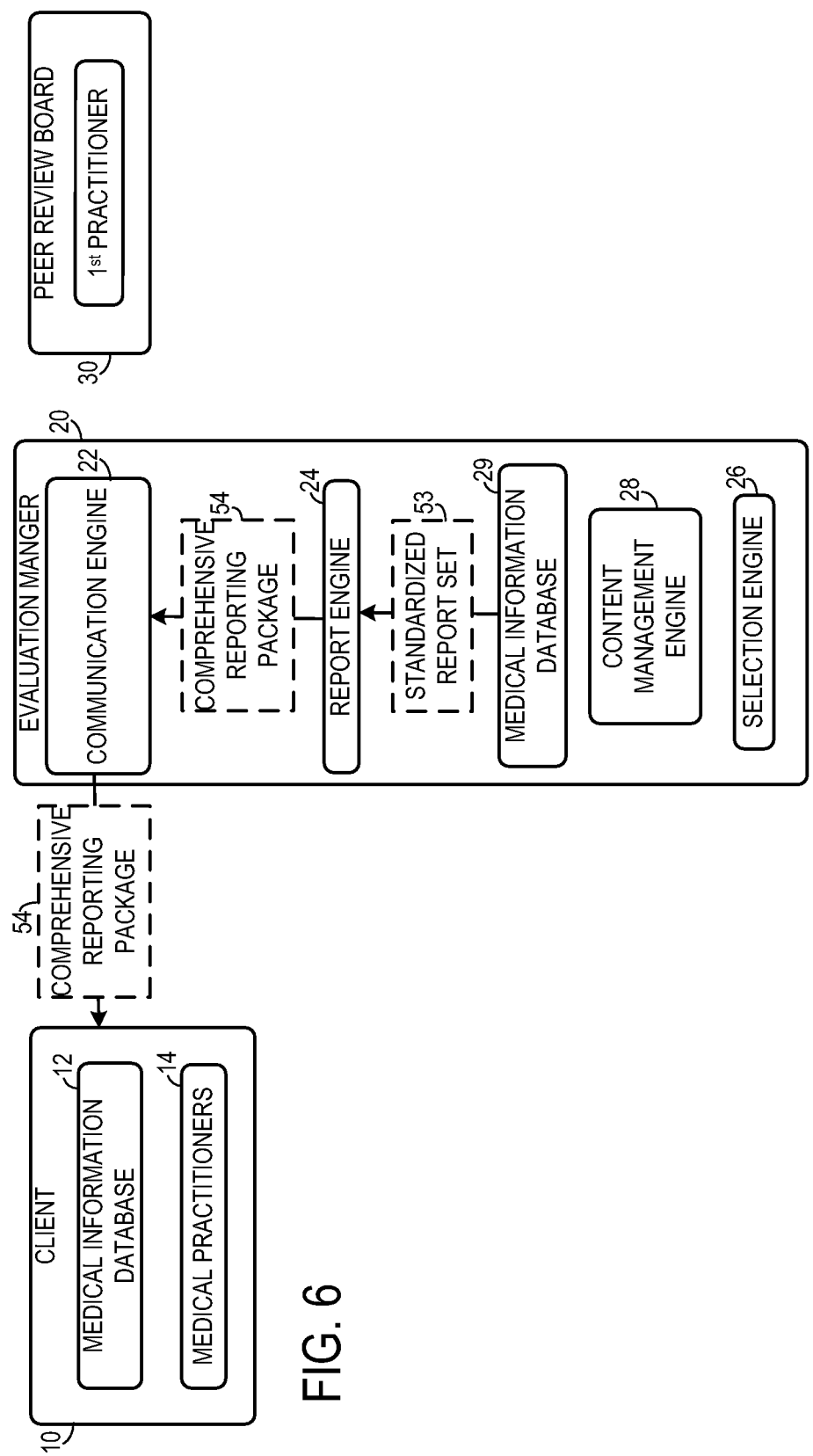

In some examples, the standardized report may be sent to the client as described above. In other examples, a plurality of reports may be generated before the standardized report in sent to the client. The plurality of standardized reports may be generated through repetition of the workflow diagrams illustrated in FIGS. 2-5. After two or more standardized reports have been generated, the standardized reports may be stored and aggregated in the manager-side medical information database, forming a set of standardized reports 53. The standardized report set may be sent to report engine 24 to generate a comprehensive reporting package 54, as shown in FIG. 6.

Comprehensive reporting package 54 may include aggregate reporting charts evaluating a level of performance two or more medical practitioners, benchmarking a medical practitioner's level of performance against other medical practitioners, which may be external to the client. The aggregate reporting charts may further include evaluation of a group of medical practitioners, a health care organization, a health care facility, etc., based on aggregated levels of performance for a plurality of medical practitioners, allowing the performance various groups included in the health care organization to be benchmarked.

Figure 10:
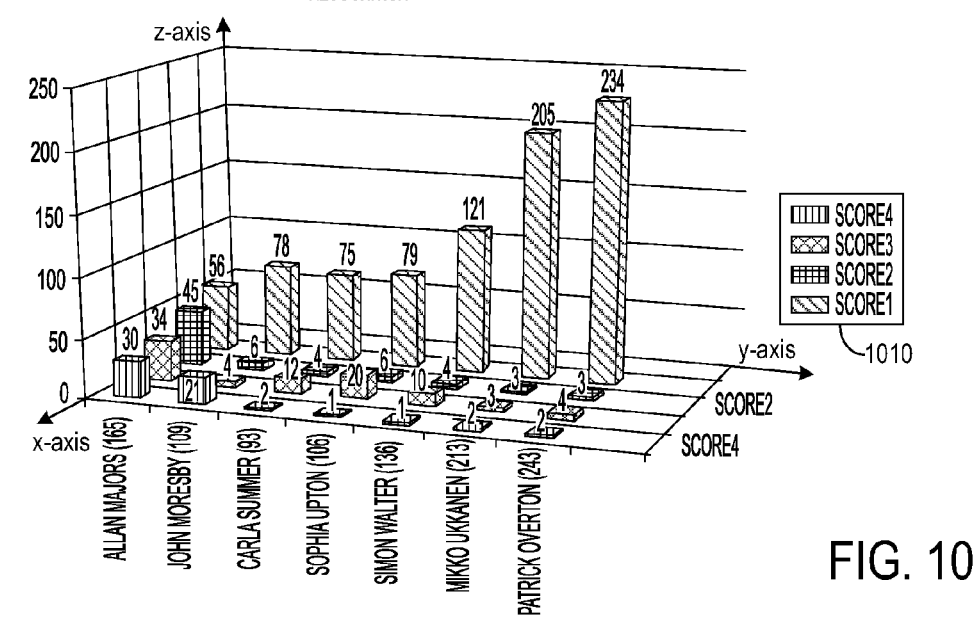

In one example, an aggregate reporting chart may include a client summary reporting chart. An exemplary client summary reporting chart is illustrated in FIG. 10. The client summary reporting chart may graphically illustrate various levels of performance corresponding to a plurality of medical practitioners and/or a specific treatment/procedure. In some examples, the medical practitioners may have the same specialty. The y-axis represents the evaluated medical practitioners. The x-axis represents the level of performance of the medical practitioner. The z-axis represents the number of cases performed by each medical practitioner for each level of performance. Again the level of performance may be coded, such as through the use of color-coding, allowing the graph to be easily deciphered. The correspondence between the level of performance and the color coding is shown in window 1010. It should be appreciated that although the reports are illustrated as bar graphs, other reports may be used, including but not limited to pie charts, line graphs, tables, etc.

Another example of an aggregate reporting chart is a location analysis reporting chart. The location analysis report may include aggregated levels of performance for a two or more facilities (e.g. hospitals) included in the health care organization. An exemplary location analysis reporting chart is illustrated in FIG. 11. The location of the hospital is given on the x-axis. The percentage of total procedures according to the level of performance is given on the y-axis. Again the level of performance is color coded, allowing the graph to be easily deciphered. The correspondence between the levels of performance and the color coding is shown in window 1110.

In some examples, such as where the client (e.g. health care organization) includes a large number of facilities, such as hospitals, the aggregate reporting chart may include a regional reporting chart, depicting aggregated levels of performance. The levels of performance may correspond to the regional groups of facilities, as shown in FIG. 12. The specific region within the health care organization is given on the x-axis. In this example, the regions may include a western region, eastern region, southern region, and northern region. However it can be appreciated that additional or alternative regions may be evaluated. The y-axis represents the percentage of total procedures performed. The bars associated with each region may be color coded according to the level of performance in the region. The correspondence between the level of performance and the color coding is shown in window 1210.

Another exemplary aggregate reporting chart includes a time-based reporting chart showing aggregated levels of performance corresponding to periods of time. FIG. 13 illustrates an example of a time-based reporting chart. The y-axis represent the time period under evaluation. The time periods may be quarterly. The z-axis represents the number times the treatments/procedures were performed. The x-axis represents the level of performance, which is color coded. The correspondence between the level of performance and the color coding is shown in window 1310.

Additionally, as a further example, an aggregate reporting chart may include a chart illustrating the level of performance of a medical practitioner in a specific specialty corresponding to a specific treatment/procedure, as illustrated in FIG. 14. The y-axis represents the medical practitioner. The z-axis represents the number times the treatment/procedure was performed. The x-axis represents the level of performance, which is color coded. The correspondence between the level of performance and the color coding is shown in window 1410.

After generation of the comprehensive reporting package, including one or more of the aggregate reporting charts, the package may be sent to the client, as shown in FIG. 6. When a web-based communications system is used the client may view the aggregate reporting package, online. In some examples, the report is converted into a viewable format, such as a Portable Document Format PFD, and then sent to the client. Additionally, the comprehensive reporting package may be sent to the manager-side medical information database, as illustrated in FIG. 6. To maintain the anonymity of the peer review board, personal information corresponding to the medical practitioners included in the peer review board may be deleted from the reporting package before it is sent to the client and/or stored in the manager-side medical information database. In some examples, when a web-based communications system is used, access to the peer review board identification information may be blocked via a suitable method.

Further in one example, when a network or web-based communications system is used, the client may be able to access the manager-side medical information database and dynamically produce reporting charts according to various parameters. The parameters may include specialty, practitioner, hospital location, hospitals region, range of dates, procedure, treatment, etc. As such, the client may be able to generate aggregate reports tailored to clients needs, such as those described above.

Figure 15:
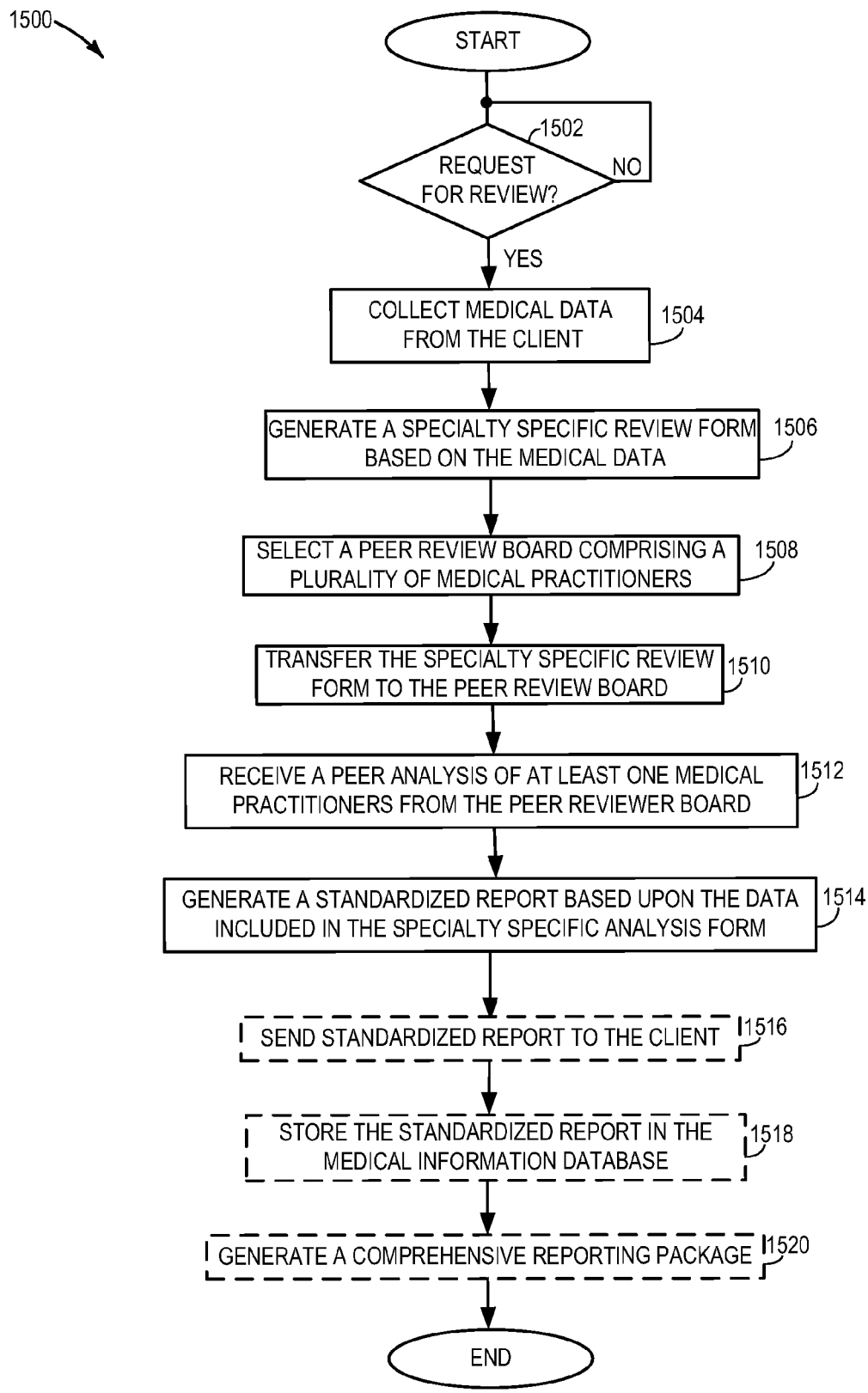
FIG. 15 illustrates a method which may be used to generate a standardized report.

FIG. 15 illustrates a method 1500 which may be used to evaluate the performance of at least one medical practitioner associated with the client. In some examples, the client may be a health care organization, hospital, ambulatory surgery center, surgical group, etc. Method 1500 may be implemented using the systems and sub-systems described above, but alternatively may be implemented using other systems and sub-systems.

In some examples, at 1502, it is determined if a request for a review of a medical practitioner has been made by the client. If a request has not been made, the method may return to the start or alternatively end.

However, if a request for a review has been made, the method may advance to 1504, where medical data is collected from the client. The method then proceeds to 1506, where a specialty specific review form, based on the collected medical data from the client, is generated.

Next the method proceeds to 1508, where a peer review board, comprising one or more medical practitioners is selected. In some examples, the peer review board selection may be based on the specialty of at least one medical practitioner under review. Next the method advances to 1510, where the specialty specific review form is transferred to the peer review board. At 1512, a peer analysis of at least one of the medical practitioners from the peer review board is received by the client, the peer analysis including a completed specialty specific review form.

The method then proceeds to 1514, where a standardized report evaluating a level of performance of at least one medical practitioner, based upon data included in the specialty specific review form, is generated. In some examples, the standardized report may benchmark the medical practitioner's level of performance against other practitioner's level of performance.

In some examples, the method may proceed to 1516, where the standardized report is transmitted to the client, which may be transmitted electronically and/or viewed online via a web-based communications system. Further in some examples, the method may proceed to 1518, where the standardized report is stored in the manager-side medical information database. The method may then proceed to 1520, where a comprehensive reporting package is generated, the comprehensive reporting packing including a plurality of aggregate reports benchmarking the medical practitioner's level of performance. Subsequent to 1520, the method ends, or alternatively returns to the start.

Figure 16:
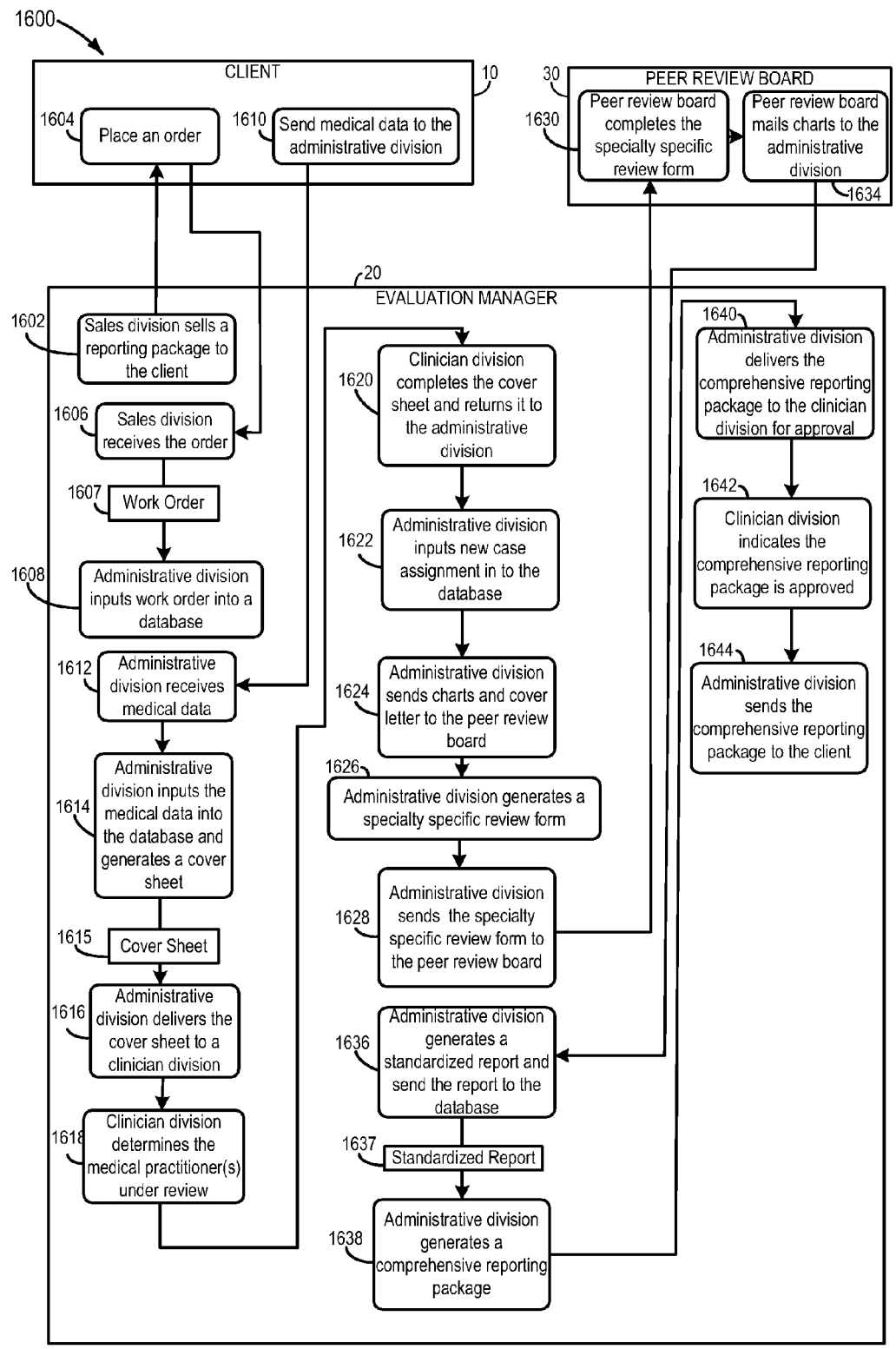
FIG. 16 illustrates an in depth procedure which may be used to generate a standardized report.

FIG. 16 further illustrates a detailed medical practitioner peer review system and method 1600. It should be appreciated that FIG. 16 is provided as an example and the disclosure is not intended to be limited as to this example. Initially, at 1602, a sales division included in the evaluation manager may sell a reporting package to client 10.

In some examples, at 1604, the client may place an order. Placing an order may include sending a retainer to the evaluation manager. Next, at 1606, the sales division may receive the order from the client and generate a new work order 1607. The work order may include a request for a review of one or more medical practitioners. The work order may then be sent to an administrative division included in the evaluation manager. The administrative division may include an operations team comprising a plurality of staff and/or software. The operations team may facilitate distribution of medical data to various entities (e.g. sub-systems, divisions, personnel) which are included in the evaluation manager. In some examples, the operations team may be included in content management engine 28, described above.

Next, at 1608 the administrative division may input the work order into a database. A suitable database may be used, such as the manager-side medical information database. At 1610, the client may send the medical data which may include medical information, such as charts, analyses, diagnoses, etc., to the administrative division. As previously discussed, the medical data may be sent according to a scheduling algorithm. Next at 1612, the administrative division may receive the medical data. At 1614 the administrative division may input the medical data into manager-side medical information database 29, and generate a cover sheet 1615 associated with a specific review being performed. In some examples, the cover sheet may be in a suitable relation database management system (e.g. SQL server).

In some examples, at 1616, the administrative division may deliver the medical data and the cover sheet to a clinician division. The clinician division may include a plurality of doctors employed or associated with the evaluation manager. The clinician division may be included in selection engine 26, discussed above.

Next at 1618, the clinician division may determine the type of medical practitioner to evaluate the medical practitioner under review. The aforementioned determination may take into account various factors, such as the experience level of the medical practitioner under review, the specialty and/or field of the medical practitioner under review, the treatments performed by the medical practitioner under review, etc. Additionally, the clinician division may also determine the due date of the standardized report and/or the comprehensive reporting package.

In some examples at 1620, the clinician division may complete the cover sheet and return it to the administrative division. At 1622, the administrative division may input a new case assignment into the database.

Next at 1624, the administrative division may send the charts and/or cover letter to the peer review board. In some examples, the charts and/or cover letter may be emailed to the peer review board. At 1626, the administrative division generates a specialty specific review form 1627 for the peer review board. In some examples, the specialty specific review form may be in a suitable spreadsheet format, such as Microsoft Excel.

At 1628 the administrative division may send and/or transmit the specialty specific review form to the peer review board. The peer review board may complete the specialty specific review form and send it back to the administrative division at 1630 and 1632 respectively. The administrative division may receive the completed specialty specific review form and upload the form into the database.

Next, at 1636, the administrative division may generate a standardized report 1637 evaluating a level of performance of at least one medical practitioner under review. The administrative division, at 1638, may generate a comprehensive reporting package, including aggregate reports, such as the reporting charts illustrated in FIGS. 8-14.

In some examples, at 1640, the administrative division may deliver the comprehensive reporting package to the clinician division for approval. Next, at 1642, the clinician division may indicate to the administrative division that the peer review, including the comprehensive reporting package, is approved. Lastly, at 1644, the administrative division may send the comprehensive reporting package to the client. In some examples, a hardcopy of the comprehensive reporting package may be mailed to the client. However, in other examples, the comprehensive may be sent and/or viewed over a web-based or network-based communications system.

Figure 17C:
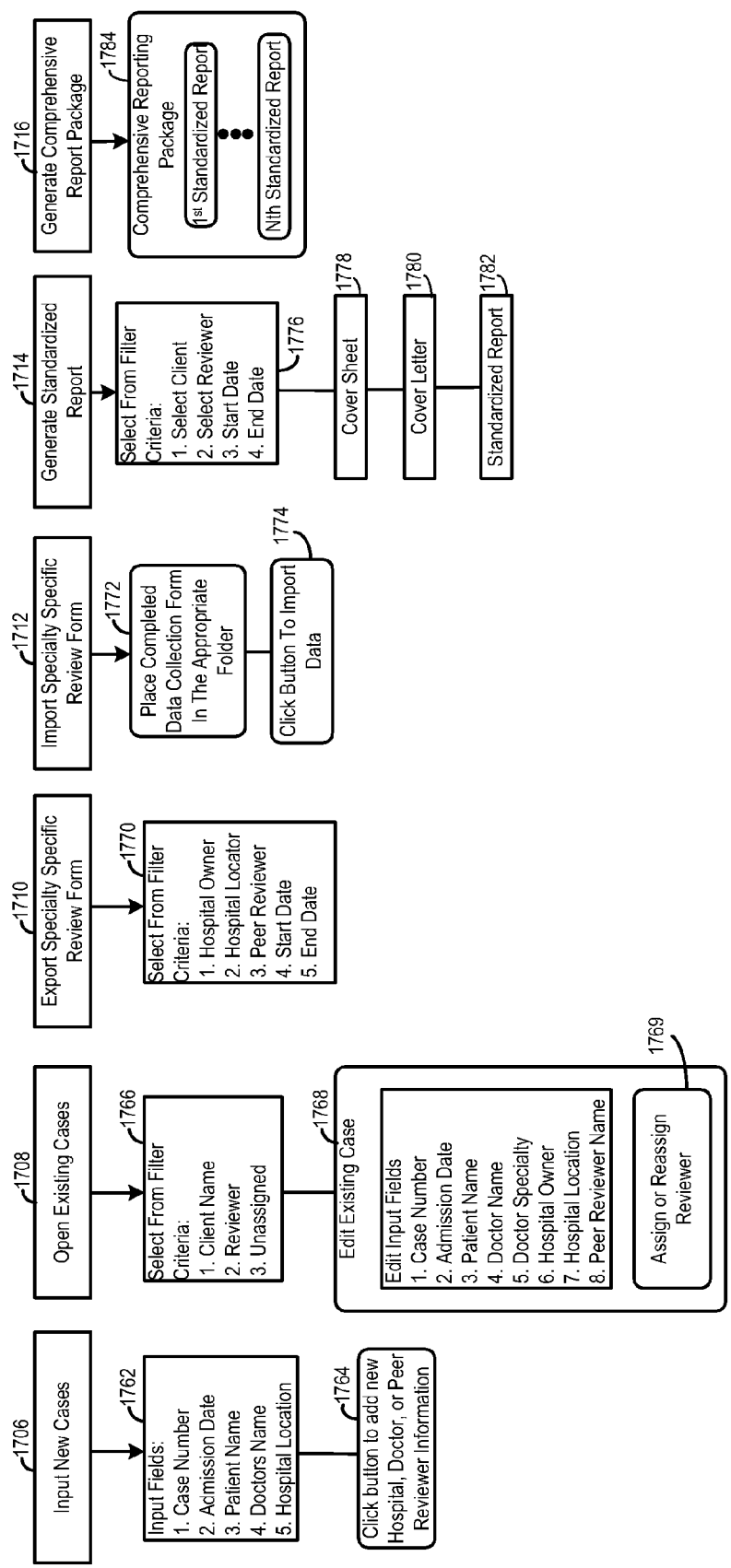

FIGS. 17A-17C illustrates an exemplary embodiment of a management application 1700 and its corresponding architecture. In some examples, the management application may be used by various sub-systems in evaluation manager 20, to navigate through as well as manage medical data in the evaluation manager. However, it should be appreciated that other suitable applications or methods may be used to manage medical data in the evaluation manager. The medical data managed by the management application may include medical data stored in the manager-side medical information database, such medical data included in a plurality of standardized reports as well as medical data gathered from client 10. The management application may be adapted to perform a number of functions via user interaction. The functions may include: managing hospitals, practitioners, and reviewers information, inputting new cases, opening existing cases, exporting a specialty specific review form, importing a specialty specific review form, generating standardized reports, and generating a comprehensive reporting package. In this way, the management application may be used by the evaluation manager to efficiently manage a large amount of medical data.

As shown in FIG. 17A, the management application may include a main menu 1702. The main menu may present a number of graphical elements in a User Interface (UI), facilitating access to the various sub-menus. As examples, the sub-menus may include: a hospital, practitioner, and reviewer management sub-menu 1704, a case input sub-menu 1706, an existing case sub-menu 1708, a specialty specific review form export sub-menu 1710, a specialty specific review form import sub-menu 1712, a standardized report sub-menu 1714, and a comprehensive reporting package sub-menu 1716.

FIG. 17B illustrates a detailed view of hospital, practitioner, and reviewer management sub-menu 1704. Sub-menu 1704 may allow a user (or in some examples a client) to manage medical information pertaining to a specific, hospital, practitioner, and/or reviewer. The users may be included in the administrative division. A specialty window 1618 may be presented within the sub-menu, allowing a user to access an existing specialty, included in the medical database. In some examples, a graphical element 1720, such as a drop down list, may be presented. Graphical element 1720 may allow the user to select a pre-existing specialty from a list. Upon selection of a specialty, a specialty information window 1722 may be displayed. In one example, a user may be allowed to modify the displayed data corresponding to the specialty of the medical practitioner. The specialty information window includes a field 1724 may prompt the user to add one or more related treatments and/or a field 1726 prompting the user to add one or more related quality criteria corresponding to the new specialty. It can be appreciated that in other examples, alternate configurations of the hospital, practitioner, and reviewer management sub-menu 1704, may be used.

In some examples, the hospital, practitioner, and reviewer management sub-menu 1904 may further include a hospital access window 1728 allowing a user to access data pertaining to an existing hospital. The user may be able to select the hospital from a list in field 1730. Upon selection of a hospital, the information relating to the specially may be displayed. In one example, a user may be allowed to modify the displayed data corresponding to the hospital. Additionally, a graphical element 1732 may be presented, facilitating the addition of a new hospital into the manager-side medical information database 29. When adding a new hospital into the manager-side medical information database various fields 1734 may be displayed, prompting the user to enter information such as the hospital's name, hospital's location, practitioners employed by the hospital, etc.

In some examples, the hospital, practitioner, and reviewer management sub-menu 1704 may further include a practitioner access window 1736, allowing a user to access information pertaining to an existing medical practitioner. The user may be able to select the practitioner from a list in field 1738 or add a new practitioner in field 1740. In some examples, when adding a new practitioner the user may be prompted in field 1742 to input the practitioner's name, hospital location, and the owner of the hospital. Further, the user may be prompted to select the practitioner's specialty in field 1744.

The hospital, practitioner, and reviewer management sub-menu 1704 may further include a peer reviewer access window 1746, allowing a user to access information pertaining to an existing peer reviewer. A peer reviewer may be a medical practitioner included in a peer review board. The user may be able to select the peer reviewer from a list in field 1748 or add a new peer reviewer in field 1750. In some examples, when adding a new peer reviewer the user may be prompted to add the reviewer's name in field 1752 and email as well as select the reviewer's specialty in field 1754.

The hospital, practitioner, and reviewer management sub-menu may further include a treatment access window 1756, allowing a user to access information pertaining to a type of treatment. The user may be able to select a type of treatment from a list in field 1758. After selection of the treatment, the user may be prompted to add one or more related complications in field 1760.

FIG. 17C illustrates an example of a case input sub-menu 1706, existing case sub-menu 1708, review form export sub-menu 1710, review form import sub-menu 1712, standardized report sub-menu 1714, and comprehensive reporting package sub-menu 1716. The case input sub-menu allows a user to input data corresponding to a new case into the manager-side medical information database. In some examples, the case input sub-menu may include input fields 1762 prompting the user to input case information, such as a case number, an admission date, a patient's name, a practitioner's name, and/or a hospital location. In one example, an input request 1764 may be presented, allowing a user to transfer the information into the medical database once the data entries have been completed.

In some examples, the existing case management sub-menu allows a user to open and view data pertaining to an existing case included in the medical database. The sub-menu may include a filter 1766 allowing a user to narrow down a list of cases. The filter may include criteria such as a client's name, reviewer, and the assignment status. A reviewer may be a medical practitioner included in the peer review group. Once the existing case has been selected an editing window 1768 may be displayed. The editing window may include one or more of the following input fields: case number, admission date, patient name, practitioner name, practitioner specialty, hospital owner, hospital location, and peer reviewer's name. An input request 1769 may be displayed, allowing a reviewer to be assigned or re-assigned.

In some examples, the specialty specific review form generation sub-menu may allow a user to select and export a specialty specific review form, corresponding to a specific case, to various recipients, such as the peer review board 30. The sub-menu may include a filter 1770 allowing a user to narrow down a list of cases for selected for exportation of a specialty specific review form. The filter may include criteria, such as the owner of the hospital, location of the hospital, name of the peer reviewer, start date of the case or procedure, and the end date of the case or procedure. Once the case has been selected a specialty specific review form may be generated and sent to the intended recipients, such as the peer review board. The specialty specific review form may be in a suitable format, such as a Microsoft Excel format designed for peer input.

Continuing with FIG. 17C, the specialty specific review form importing sub-menu may prompt a user to place a specialty specific review form, complete by the peer review board, in an appropriate location include in the management application, such as a folder included in the medical database, shown in window 1772. In some examples, the completed specialty specific review form may be included in the peer analysis 48 generated by the peer review board, discussed above. Further, an input request 1774 may be included in the specialty specific review form importing sub-menu, allowing the data included in the inputs fields to be imported.

In some examples, the peer assignment sub-menu allows a user, such as a peer reviewer, to generate a number of documents corresponding to one or more cases, allowing the peer reviewers to easily view their workload as well as view instructions for review. The sub-menu may include a filter 1776 allowing a user to filter and select one or more cases from a list of cases. The filter may include criteria such as the client's name, the reviewer's, the start date of the case, and the end date of the case. In some examples, the aforementioned criteria may populate a multi-selection list window corresponding to a list of filtered cases. Following filtration, a user can select one or more cases included in a displayed list of cases.

Once one or more cases have been selected a number of documents may be generated, in some examples. The documents may include a cover sheet 1778. The cover sheet may include information relating to one or more cases, allowing a medical practitioner included in the peer review board (i.e. reviewer) to determine the case(s) under review. The documents may further include a peer instruction cover letter 1780. The peer instruction cover letter may include a summary of one or more cases to be reviewed and instructions for review. Still further the documents may include a read-only standardized medical practitioner report 1782, allowing a reviewer to view an exemplary standardized report.

Continuing with FIG. 17C, the comprehensive reporting package sub-menu may include a number of sections viewable by client 10 as well as the evaluation manager 20, allowing the client to view a comprehensive reporting package 1784. In some example, comprehensive reporting package may be similar to comprehensive reporting package 54, shown in FIG. 6. In other examples, comprehensive reporting package 1784 may be another suitable reporting package. The comprehensive reporting package may include aggregate reports. Various reporting charts which may be included in the comprehensive reporting package are shown in FIGS. 10-14.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein.

Inventions embodied in various combinations and subcombinations of features, functions, elements, and/or properties may be claimed in a related application. Such claims, whether they are directed to a different invention or directed to the same invention, whether different, broader, narrower or equal in scope to any original claims, are also regarded as included within the subject matter of the inventions of the present disclosure.

The invention claimed is:

1. A method for evaluating performance of at least one medical practitioner associated with a client, the method executable on a computing device including memory and a processor comprising:
    generating a medical specialty specific review form including medical review criteria in a field corresponding to a specified medical specialty based on medical data collected from the client where the medical review criteria correspond to specific procedures and treatments frequently carried out in the specified medical specialty;
    selecting a peer review board based on a specialty of the at least one medical practitioner under review;
    subsequently transferring the medical specialty specific review form to the peer review board;
    receiving a peer analysis of the at least one medical practitioner from the peer review board, the peer analysis including a completed medical specialty specific review form; and
    generating a standardized report evaluating a level of performance of the at least one medical practitioner based upon data included in the peer analysis;
    wherein the steps of generating a medical specialty specific review form, selecting a peer review board, subsequently transferring the medical specialty specific review form to the peer review board, receiving a peer analysis, and generating a standardized report are stored in memory executable by the processor on the computing device and where the steps are performed by the processor of the computing device.

2. The method of claim 1, wherein the medical data is collected from the client pro-actively, according to a scheduling algorithm.

3. The method of claim 1, wherein the specialty specific peer review form includes a review form with medical review criteria including at least one of pre-procedure evaluation and indications, procedure technique, complications/timely recognition, post-procedure care, and utilization of ancillary services and consultants, each medical review criteria tailored to the specified medical specialty, and where a plurality of specialty specific review forms are generated including a first form including a first set of fields tailored to a first medical specialty, and a second form including a second set of fields at least some of which are different from the first set of fields, the second set of fields tailored to a second medical specialty different from the first medical specialty, and where the tailored fields are based on the medical specialty for which the form is generated.

4. The method of claim 1, further comprising transferring the medical specialty specific review form via a web-based network.

5. The method of claim 1, wherein the standardized report comprises a graphical depiction of the level of performance of the at least one medical practitioner.

6. The method of claim 5, wherein the graphical depiction is color-coded according to the level of performance of the at least one medical practitioner.

7. The method of claim 1, further comprising storing the standardized report in a medical information database.

8. The method of claim 1, wherein the standardized report is generated based on aggregated data from a medical information database, benchmarking the at least one medical practitioner's level of performance.

9. The method of claim 1, further comprising generating a comprehensive reporting package comprising aggregate reports benchmarking a performance of a medical facility associated with the client.

10. An evaluation manager for a client executed on a computing device including memory and a processor, the evaluation manager comprising:
- a computing device including memory and a processor;
- a communications engine, stored in memory executable by the processor of the computing device, adapted to facilitate communication between the client, the evaluation manager, and a peer review board;
- a selection engine, stored in memory executable by the processor of the computing device, adapted to select the peer review board including one or more medical practitioners;
- a content management engine, stored in memory executable by the processor of the computing device, adapted to selectively gather medical data from the client, generate a medical specialty specific review form including medical review criteria in a field corresponding to a specified medical specialty, where the medical review criteria include at least one of pre-procedure evaluation and indications, procedure technique, complications/timely recognition, post-procedure care, and utilization of ancillary services and consultants, the medical review criteria tailored to specific procedures and/or treatments commonly carried out in the specified medical specialty, and send the medical specialty specific review form to the peer review board; and
- a report engine, stored in memory executable by the processor of the computing device, adapted to receive a completed medical specialty specific review form from the peer review board as well as aggregate data from a medical information database, the report engine further adapted to generate a comprehensive reporting package including a plurality of reports evaluating a level of performance of two or more medical practitioners associated with the client.

11. The evaluation manager of claim 10, wherein the client is a health care organization and the selected medical practitioners are external to the health care organization.

12. The evaluation manager of claim 10, wherein the selectively gathered medical data corresponds to a specialty of the medical practitioner and the selectively gathered medical data is pro-actively gathered in response to a request from the client.

13. The evaluation manager of claim 10, wherein the communications engine is web-based and the comprehensive reporting package benchmarks the two or more medical practitioners' levels of performance against other medical practitioners' levels of performance.

14. The evaluation manager of claim 13, wherein the comprehensive reporting package is dynamically modified by the client according to parameters including one or more of a specialty of the medical practitioner under review and treatments and/or procedures performed by the medical practitioner under review.

15. The evaluation manager of claim 10, wherein the medical information database can be sorted by the evaluation manager according to one or more of a specialty, a hospital, a hospital group, a procedure, and a treatment.

16. A system for generating a standardized evaluation of at least one medical practitioner based on a peer analysis, the system comprising:
- a computing device having memory and a processor;
- a web-based communications engine, stored in memory executable by the processor of the computing device, communicatively linking a client, an evaluation manager, and a peer review board;
- a selection engine, stored in memory executable by the processor of the computing device, adapted to select a peer review board based on a specialty of the at least one medical practitioner;
- a content management engine, stored in memory executable by the processor of the computing device, adapted to selectively gather medical data from the client, generate a medical specialty specific review form including medical review criteria in a field corresponding to a specified medical specialty, where the medical review criteria are tailored to specific procedures and/or treatments frequently carried out in the specified medical specialty, and transfer the medical specialty specific review form to the peer review board where the medical specialty specific review form is completed as part of a peer analysis; and
- a report engine, stored in memory executable by the processor of the computing device, adapted to generate a standardized evaluation of the at least one medical practitioner based on the peer analysis generated by the peer review board.

17. The system of claim 16, wherein the standardized evaluation includes a plurality of graphical depictions corresponding to the specialty of the at least one medical practitioner.

18. The system of claim 16, wherein the report engine is adapted to generate a comprehensive reporting package evaluating a level of performance of two or more medical practitioners.

19. The system of claim 16, wherein the standardized evaluation is further based on data from a medical information database.

20. The system of claim 16, wherein the content management engine includes a culling system adapted to filter extraneous information from the medical data and form one or more data sets.

* * * * *